United States Patent
Ueda et al.

(10) Patent No.: US 7,252,653 B2
(45) Date of Patent: Aug. 7, 2007

(54) LIQUID INJECTION NEEDLE AND LIQUID INJECTION DEVICE

(75) Inventors: Mieko Ueda, Kanagawa (JP); Tetsuya Ooyauchi, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 650 days.

(21) Appl. No.: 10/470,007

(22) PCT Filed: Jan. 25, 2002

(86) PCT No.: PCT/JP02/00550

§ 371 (c)(1), (2), (4) Date: Jul. 23, 2003

(87) PCT Pub. No.: WO02/058769

PCT Pub. Date: Aug. 1, 2002

(65) Prior Publication Data

US 2004/0078008 A1    Apr. 22, 2004

(30) Foreign Application Priority Data

Jan. 25, 2001  (JP)  ............................. 2001-016444
Dec. 26, 2001  (JP)  ............................. 2001-393688

(51) Int. Cl.
*A61M 5/32*  (2006.01)
(52) U.S. Cl. ...................................................... 604/272
(58) Field of Classification Search ........ 604/272–274, 604/187, 264
See application file for complete search history.

(56) References Cited

U.S. PATENT DOCUMENTS

| | | | | |
|---|---|---|---|---|
| 422,436 A | * | 3/1890 | Otto | ............................. 604/273 |
| 2,187,259 A | * | 1/1940 | Barnhart | ...................... 604/117 |
| 5,364,374 A | * | 11/1994 | Morrison et al. | ........... 604/272 |
| 5,951,528 A | * | 9/1999 | Parkin | ......................... 604/239 |
| 6,537,243 B1 | * | 3/2003 | Henning et al. | ............... 604/28 |
| 6,843,783 B2 | * | 1/2005 | Ooyauchi | .................... 604/239 |
| 2003/0050602 A1 | * | 3/2003 | Pettis et al. | .................. 604/117 |

FOREIGN PATENT DOCUMENTS

| | | |
|---|---|---|
| DE | 88 02 264.1 | 8/1988 |
| GB | 542619 | 1/1942 |

OTHER PUBLICATIONS

Office Action issued on Sep. 25, 2006, in corresponding Korean Appln. No. 10-2003-7009688, together with an English Translation.

* cited by examiner

*Primary Examiner*—Kevin C. Sirmons
*Assistant Examiner*—Elizabeth MacNeill
(74) *Attorney, Agent, or Firm*—Buchanan Ingersoll & Rooney PC

(57) ABSTRACT

A liquid injection needle (10) includes a hollow needle part (2) for injecting a liquid (8) and a supporting part (3), to which the needle part (2) is fixed. The needle part (2) includes an anchoring part (22) that extends through the inside of the supporting part (3) and a puncturing part (21) that extends from the supporting part (3) for making a puncture in a living body. The puncturing part (21) has a distal side outer diameter equal to or greater than 0.1 mm and equal to or less than 0.25 mm, and a proximal side outer diameter than the distal side outer diameter.

9 Claims, 9 Drawing Sheets

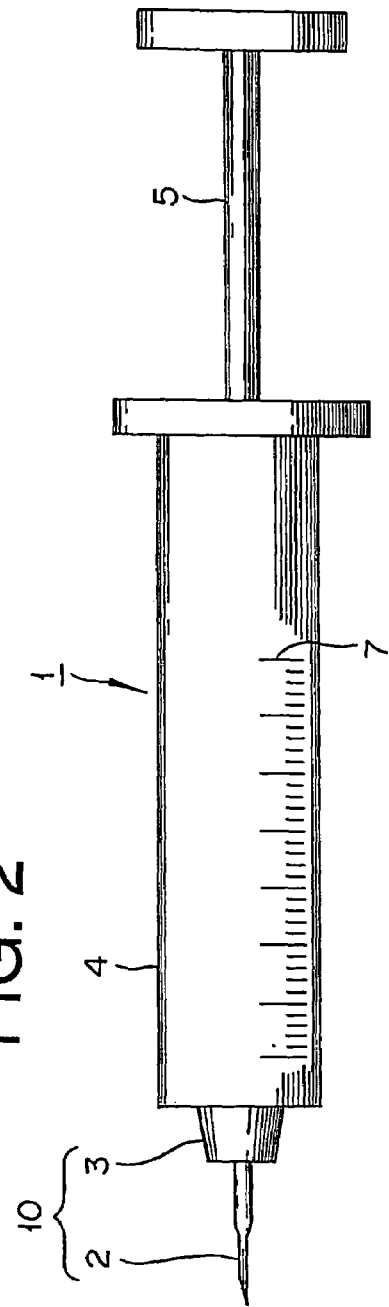
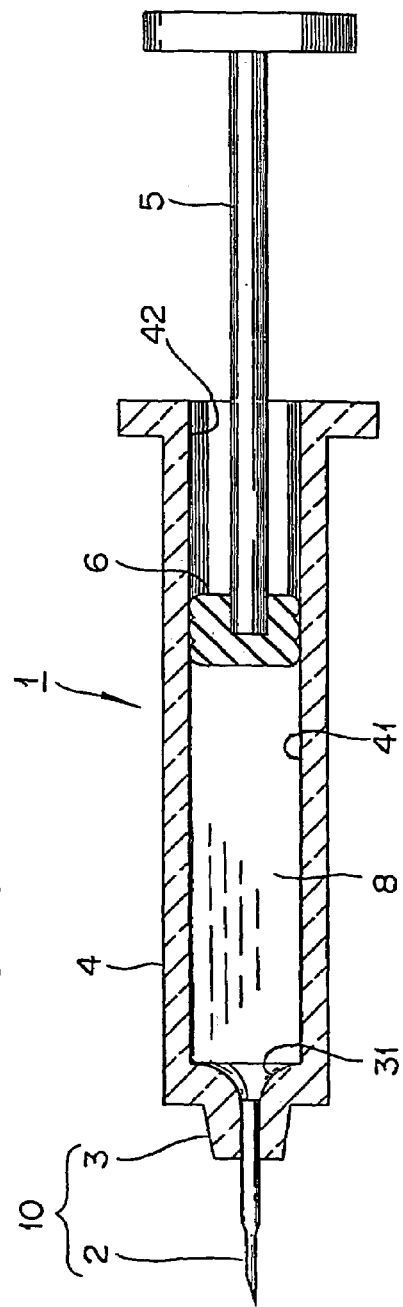

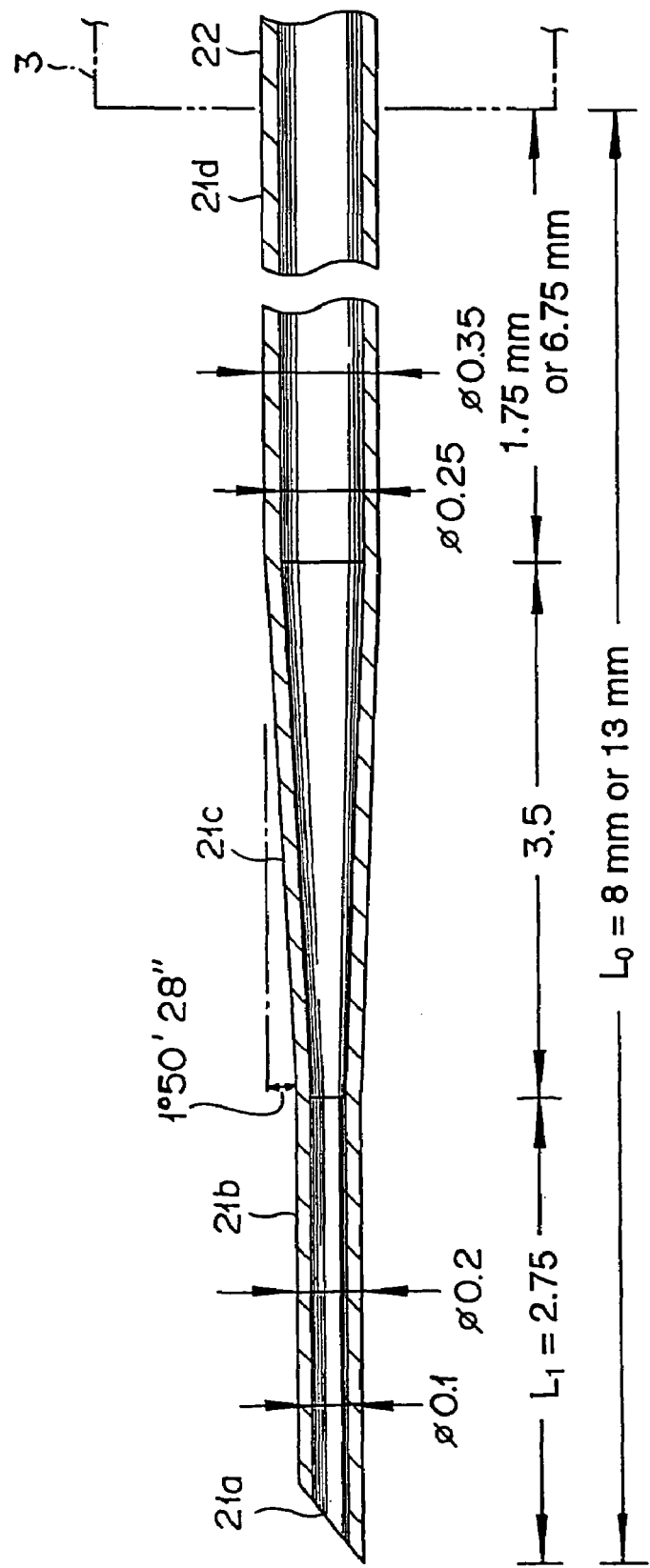

FIG. 12

| | EXAMPLE | | | | | | | | | | | |
|---|---|---|---|---|---|---|---|---|---|---|---|---|
| | 2 | 3 | 4 | 5 | 6 | 7 | 8 | 9 | 10 | 11 | 12 | 13 |
| TOTAL LENGTH L₀ OF PUNCTURING PART 21 [mm] | 13 | 13 | 13 | 13 | 13 | 13 | 13 | 13 | 13 | 13 | 13 | |
| LENGTH L₁ OF DISTAL END 21b [mm] | 2.75 | 2.75 | 2.75 | 2.75 | 2.75 | 2.75 | 2 | 4 | 1 | 2.75 | 2 | |
| OUTER DIAMETER OF PROXIMAL END 21d [mm] | 0.35 | 0.35 | 0.35 | 0.35 | 0.35 | 0.35 | 0.35 | 0.35 | 0.35 | 0.35 | 0.35 | |
| INNER DIAMETER OF PROXIMAL END 21d [mm] | 0.25 | 0.25 | 0.25 | 0.25 | 0.25 | 0.25 | 0.25 | 0.25 | 0.25 | 0.25 | 0.25 | |
| OUTER DIAMETER OF DISTAL END 21b [mm] | 0.18 | 0.2 | 0.2 | 0.2 | 0.2 | 0.2 | 0.2 | 0.2 | 0.2 | 0.22 | 0.22 | |
| INNER DIAMETER OF DISTAL END 21b [mm] | 0.1 | 0.1 | 0.1 | 0.1 | 0.1 | 0.1 | 0.1 | 0.1 | 0.1 | 0.12 | 0.12 | |
| LENGTH OF MIDDLE PART 21c [mm] | 3.5 | 3.5 | 3.5 | 3.5 | 3.5 | 3.5 | 5 | 4 | 3.5 | 3.5 | 5 | |
| FIRST GRINDING ANGLE α [°] | 8.5 | 8.5 | 8.25 | 8.25 | 8.5 | 8.5 | 8.5 | 8.5 | 8.5 | 8.5 | 8.5 | |
| SECOND GRINDING ANGLE φ [°] | 17 | 17 | 15 | 16.75 | 13 | 18 | 17 | 17 | 17 | 17 | 17 | |
| CROSS SECTIONAL ANGLE γ [°] | 130 | 130 | 120 | 120 | 140 | 129 | 130 | 130 | 130 | 130 | 103 | |
| STICKING RESISTANCE [gf] | 5.4 | 5.4 | 6 | 6.2 | 6.4 | 6.4 | 5.5 | 5.5 | 5.5 | 7.1 | 7 | |
| FLOW PATH RESISTANCE [gf] | 243 | 243 | 243 | 243 | 243 | 243 | 248 | 285 | 230 | 210 | 205 | |

LIQUID INJECTION NEEDLE AND LIQUID INJECTION DEVICE

This application is the National Phase of International Application PCT/JP02/0050, filed Jan. 25, 2002, which designated the United States. International Application PCT/JP02/00550 claimed priority to Japanese Application 2001-016444, filed Jan. 25, 2001, and Japanese Application 2001-393688, filed Dec. 26, 2001.

1. Technical Field

The present invention generally pertains to a liquid injection needle and a liquid injection device. More particularly, the invention relates to a liquid injection needle and a liquid injection device used for percutaneously injecting drug solutions for living bodies into living bodies intracutaneously, subcutaneously, or intramuscularly.

2. Background

An example of a known drug injection device used for injecting drug solutions into living bodies is shown in FIG. 1. The drug injection device 101 includes a needle 102 for injecting a drug solution, a supporting part 103 for supporting the needle 102, a substantially cylindrical shaped main body 104 for containing the drug, and a plunger 105 for injecting the drug contained inside the main body 104. The needle 102 consists of a hollow needle having a constant outer diameter, one end of which is firmly fixed to the supporting part 103, and is capable of communicating with the inner space of the main body 104.

However, the needle 102 has an outer diameter larger than 0.3 mm and is relatively thick. As a result, pain may result to the patient when the needle 102 punctures the living body or injects a drug solution into the living body. Also, considering the size of the needle, the thought of being punctured with the needle can cause anxiety to the patient.

Using a thinner needle to reduce the pain and/or anxiety to the patient has its own problems. For example, it is extremely difficult to fix a thin needle to the supporting part in order to assemble a drug injection device. There is also a concern that a thin needle may be unable to puncture the skin of a living body and may end up bending due to its lack of physical strength.

Moreover, a thin needle naturally has a small inner diameter, and so an excessively large force may be required to suck the drug solution from a container such as a vial or inject the drug into the living body. Thus, a potential problem exists in that a thin needle may require a large force for sucking the drug solution from a container or injecting the drug into the living body.

Drug injection devices to be used for percutaneous self-administration of insulin solutions (the solutions containing insulin) by diabetic patients are available on the market. The thinnest outer diameter available on such drug injection devices is 0.254 mm (31 G (Gage)). The "Gage" is a number based on the B.W.G. (Birmingham Wire Gage) standard.

Unfortunately, the injection resistance felt in injecting drug solutions using a 31 G needle is substantially large. This is due to the fact that the injection resistance increases theoretically in inverse proportion to the fourth power of the needle diameter.

Therefore, there is a concern that a patient with weak strength may have problem in injecting a drug solution in case of subcutaneous self-administration using a 31 G needle because the force usable for pressing the plunger of a drug injection device is poor. In such a case, the patient has no choice but to use a thicker needle, for example, a needle with an outer diameter of 0.30 mm (30 G), which causes less injection resistance, but greater pain.

Another problem in using a 31 G needle is that the insulin solution may leak through the punctured hole in the skin or from the tip of the needle. One of the causes of such a problem is the following.

A needle as thin as a 31 G needle requires a long time to complete the injection of the drug solution as it has a high injection resistance. Consequently, the patient may become impatient and pull the needle out of the skin before the entire administration amount of the drug to be delivered per injection (i.e., insulin unit) is administered subcutaneously.

The insulin unit is predetermined for each diabetic patient and it is essential to administer an exact amount per each injection. Leakage of the drug solution after injection means that an amount less than the required amount is administered, hence being unable to provide sufficient curing effect.

In the field of dental treatments, drug injection devices are used for injecting anesthetic drugs, such as lidocaine, into the patient's dental pulp. The thinnest needle available on the market for drug injection devices for dental use has an outer diameter of 0.26 mm.

A substantially high injection resistance develops when a dental needle with an outer diameter of 0.26 mm is used for injecting anesthetic drugs into dental pulps and the like. Therefore, the main body of the device and the plunger are made of metals requiring a doctor with a normal, healthy body for injecting an anesthetic drug. Thus, it is possible to inject an anesthetic drug even with such a thin needle, if a very large force is applied to the plunger.

However, because the device and the plunger are made of metal, the device is relatively heavy and difficult to handle. If injection resistance can be reduced, lighter materials such as plastics can be used to form the device and injection can be done with less force. Hence, it is possible to provide a lighter and easier to use drug injection device for dental use.

Moreover, as mentioned above, a thicker needle is not preferable as it tends to create anxiety in the patient, although it can reduce injection resistance. In other words, it is preferable to use a thinner needle to reduce or alleviate pain or anxiety to the patient in a dental drug injection device as well.

Thus, although very thin needles can reduce or alleviate pain to the patient, problems exist such as difficulty of manufacture, lack of strength and high injection resistance. Such needles are thus not practically used.

An object of the present invention is to provide a very thin liquid injection needle, and a liquid injection device equipped with such liquid injection needle, that are capable of alleviating pain to the patient, being relatively easy to manufacture, providing sufficient strength, and causing less injection resistance.

DISCLOSURE OF INVENTION

A liquid injection needle of the invention includes a hollow needle part for injecting a liquid and a supporting part to which the needle part is fixed, wherein the needle part comprises an anchoring part that extends through the inside of the supporting part and a puncturing part that extends from the supporting part for making a puncture in a living body. The puncturing part has a distal side outer diameter equal to or greater than 0.1 mm and equal to or less than 0.25 mm, and a proximal side outer diameter greater than the distal side outer diameter.

According to another aspect, a liquid injection needle includes a hollow needle part for injecting a liquid and a supporting part to which the needle part is fixed, wherein the needle part has an anchoring part that extends through the inside of the supporting part and a puncturing part that extends from the supporting part for making a puncture in a living body. The puncturing part has a proximal side outer diameter greater than a distal side outer diameter and possesses a sticking resistance equal to or less than 7 gram-force.

In accordance with another aspect, a liquid injection needle includes a hollow needle part for injecting a liquid and a supporting part to which the needle part is fixed, wherein the needle part has an anchoring part that extends through the inside of the supporting part and a puncturing part that extends from the supporting part for making a puncture in a living body. The puncturing part has a proximal side outer diameter greater than a distal side outer diameter, and the needle part has a flow path resistance equal to or less than 350 gram-force under a sustained water flow rate of 20 µl/sec.

Another aspect involves a liquid injection device provided with the above-described liquid injection needle, wherein the liquid injection device includes a main body having an internal space adapted to contain the liquid, with the supporting part being provided on one end part of the main body. The needle part of the liquid injection needle is fixed on the supporting part to communicate with the internal space.

BRIEF DESCRIPTION OF DRAWINGS

The foregoing and additional features and characteristics of the present invention will become more apparent from the following detailed description considered with reference to the accompanying drawing figures in which like reference numerals designate like elements.

FIG. 2 is a side view of a drug injection device of an embodiment according to the present invention.

FIG. 3 is a cross-sectional view of the drug injection device shown in FIG. 2.

FIG. 6 is an expanded cross-sectional view of a drug injection needle according to example 1 used for sticking resistance measurement.

FIG. 12 is a table showing the results of the sticking and flow path resistance measurement of examples 2-12.

BEST MODE FOR CARRYING OUT THE INVENTION

Figure 1:
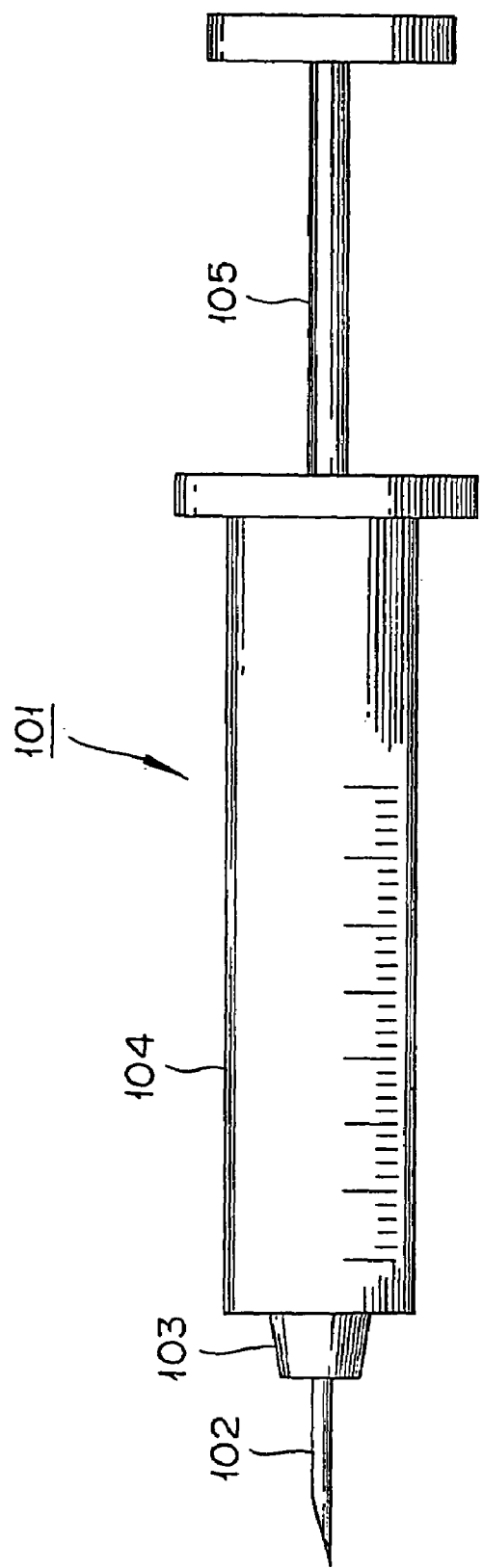
FIG. 1 is a side view of a known drug injection device.

Referring initially to FIGS. 2 and 3, a drug injection device 1 according to one embodiment includes a drug injection needle 10 and a main body 4. The drug injection needle 10 has a hollow needle part 2 possessing a special shape and a supporting part 3 to which one end of the needle part 2 is firmly fixed. The main body 4 is substantially cylindrical in shape and has an internal space 41 into which a plunger 5 is inserted allowing the plunger 5 to reciprocate longitudinally.

In general, drug solution 8 is sucked from a container such as a vial into the internal space 41 through the needle part 2, and is injected into the living body from the tip of the needle part 2 by pushing the plunger 5 into the main body 4.

The supporting part 3 located on one end (i.e., the left end in FIGS. 2 and 3) of the main body 4 has a passage 31 formed to communicate with the internal space 41 of the main body 4. The base of the needle part 2 is fixed in a liquid-tight manner to the internal surface of the passage 31. Therefore, the needle part 2 communicates with the internal space 41 of the main body 4 via the passage 31.

In the illustrated embodiment, the supporting part 3 and the main body 4 are formed integrally. However, it is also possible to form the supporting part 3 and the main body 4 separately, and fix the supporting part 3 to the end of the main body 4 by way of gluing or welding. It is also possible to detachably mount the supporting part 3 to the end of the main body 4 by way of threading or fitting.

On the other end (i.e., the right end in FIGS. 2 and 3) of the main body 4, an opening 42 is provided to insert the plunger 5 into the internal space 41. A gasket 6 is provided on the tip of the plunger 5 that fits closely into the inner wall of the main body 4. The gasket 6 serves a sealing function so that the drug solution does not leak backward when the plunger 5 moves toward the supporting part 3.

The drug solution 8 is, for example, a liquid solution, a gel or a suspension containing a drug. The device is applicable to any drug, as long as it is not a drug unsuitable for percutaneous administration.

Major drugs that can be included in this category are antibacterial drugs, antiviral drugs, vaccines, antineoplastic drugs, immunosuppressive drugs, steroid, antiinflamatory drugs, antirheumatic drugs, arthritis drugs, antihistamic drugs, antiallergic drugs, antidiabetic drugs, hormone agents such as growth hormone, bone calcium metabolic drugs, vitamins, blood products, hematopoietic drugs, antithrombotic drugs, hypolipidemic drugs, antiarrhythmic drugs, vasodilator drugs, prostaglandin, calcium antagonistic drugs, ACE inhibitors, β blockers, antihypertensive drugs, diuretic drugs, xanthine derivatives, β agonists, antasthmatic drugs, antitussive drugs, expectorants, anticholinergic drugs, antidiarrheal drugs, digestants, antiulcer drugs, cathartic drugs, hypnotic drugs, sedative drugs, antipyretic drugs, cold remedies, antiepileptic drugs, antipsychotic drugs, antidepressive drugs, antianxiety drugs, central nerve irritant drugs, parasympathetic drugs, sympathetic drugs, antiemetic drugs, central stimulants, antiparkinsonism drugs, muscle relaxants, anticonvulsants, anesthetic agents, antipruritic drugs, migraine drugs, oligonucleotides, gene drugs, etc.

Drugs that are ineffective or become less effective when orally administered, for example, peptide, protein, polysaccharide, oligonucleotide, DNA, etc., are more preferable for this application.

The injection amount of the drug solution 8 per each administration is set up equal to the single administration amount of conventional injection drugs, which is 1 ml or less in most cases, or between 0.01 and 2 ml.

The gasket 6 is made of butyl rubber, silicone rubber, elastomer, etc., and is formed by a molding process. The supporting part 3, the main body 4; and the plunger 5 are made of plastic materials such as polypropylene, and polyethylene, and formed by a molding process.

The main body 4, the supporting part 3, and the plunger 5 are made partially or totally of a transparent material so that the user can visually check the quantity of the drug solution 8 contained in the internal space 41. The surface of the main body 4 has a scale 7 so that the user can check the amount of drug solution 8 contained or injected.

Figure 4:
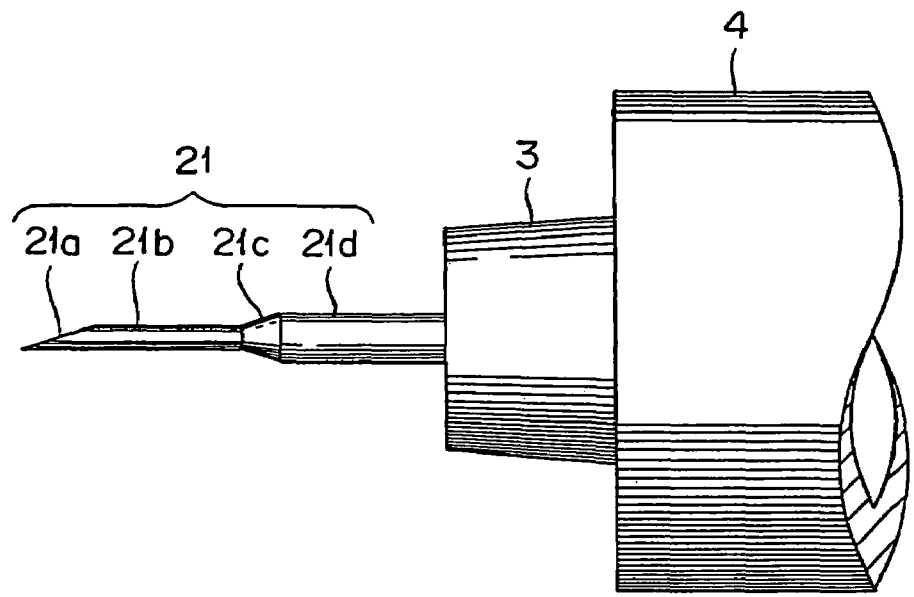
FIG. 4 is a side view of a drug injection needle of the drug injection device shown in FIG. 2.
Figure 5:
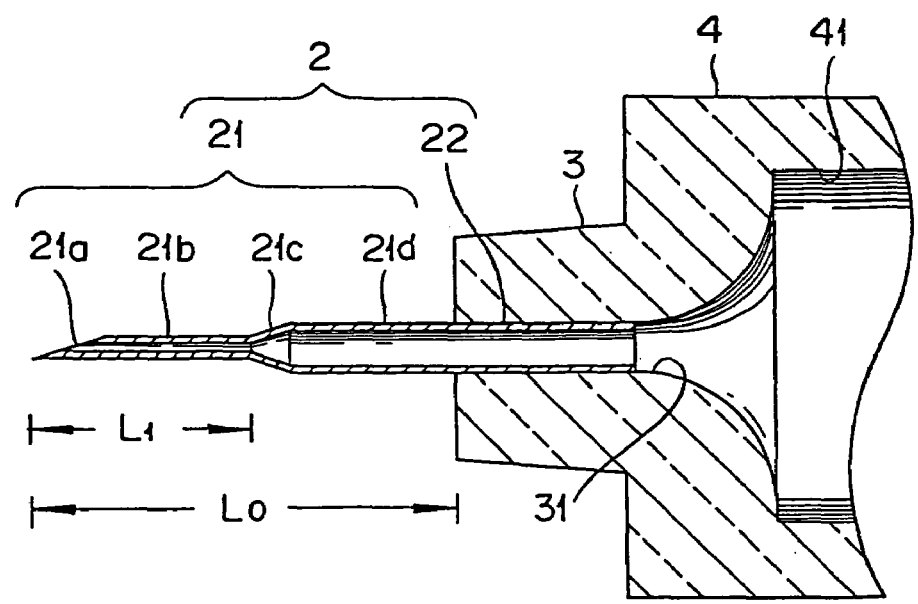
FIG. 5 is a cross-sectional view of the drug injection needle shown in FIG. 4.

The needle part 2 has a puncturing part 21 and an anchoring part 22 as shown in FIG. 4 and FIG. 5. The puncturing part 21 is an extension part protruding outward from the supporting part 3 and is adapted to be stuck into the living body. The anchoring part 22 is an extension part that extends into the inside of the supporting part 3, and connects or communicates with the passage 31 that communicates with the internal space 41 of the main body 4.

The tip of the puncturing part 21 has a slanted part 21a forming a blade surface that can be stuck into the skin. The blade surface is formed by slicing the tip at an angle.

The distal side outer diameter of the puncturing part 21, i.e., the outer diameter of the puncturing part 21 in the vicinity of the slanted part 21a should be equal to or larger than 0.1 mm and equal to or smaller than 0.25 mm, preferably equal to or larger than 0.1 mm and equal to or smaller than 0.23 mm, more preferably equal to or larger than 0.1 mm and equal to or smaller than 0.20 mm.

The upper limit of the distal side outer diameter of the puncturing part 21 is set smaller than the conventional size from the standpoint of reducing the sticking pain to the patient. The lower limit is set from the standpoint of securing the desired strength and suppressing the increase of flow path resistance during the drug solution injection. The distal side internal diameter of the puncturing part 21 is preferably equal to or larger than 0.05 mm and equal to or smaller than 0.15 mm, preferably equal to or larger than 0.05 mm and equal to or smaller than 0.13 mm, more preferably equal to or larger than 0.05 mm and equal to or smaller than 0.10 mm.

In the process of percutaneous puncture by way of a needle, nociperception is induced generally as a result of the tip of the needle advancing into the deeper area of the skin, tearing up the skin and causing irritation and damage in the nerves and veins related to the pain.

However, the distal side outer diameter of the puncturing part 21 is chosen extremely small in this embodiment. Therefore, irritation and damage in the nerves and veins caused by the slanted part 21a that punctures the skin and tears the living body are minimized. Thus, the puncturing part 21 causes almost no puncturing pain to the patient.

On the other hand, the proximal side outer diameter of the puncturing part 21 is chosen larger than the distal side outer diameter of the puncturing part 21. Therefore, strength sufficient for puncturing the living body with the puncturing part 21 can be secured. This helps prevent the user from causing an accidental breakage of the puncturing part 21 and leaving the puncturing part 21 inside the living body.

Specifically, the proximal side outer diameter of the puncturing part 21 is equal to or larger than 0.3 mm and equal to or smaller than 2 mm, more preferably equal to or larger than 0.35 mm and equal to or smaller than 1.5 mm, most preferably equal to or larger than 0.35 mm and equal to or smaller than 1 mm.

The lower limit of the proximal side outer diameter of the puncturing part 21 is chosen larger than the distal side outer diameter of the puncturing part 21 from the standpoint of aggressively reducing the flow path resistance during the drug solution injection as mentioned above. Also, the upper limit of the proximal side outer diameter of the puncturing part 21 is chosen to suppress the sticking resistance into the living body. The proximal side internal diameter of the puncturing part 21 should preferably be equal to or larger than 0.20 mm and equal to or smaller than 1.2 mm, preferably equal to or larger than 0.25 mm and equal to or smaller than 1.0 mm, more preferably equal to or larger than 0.25 mm and equal to or smaller than 0.8 mm.

The total length $L_0$ of the puncturing part 21 is preferably equal to or larger than 1.5 mm and equal to or smaller than 15 mm, more preferably equal to or larger than 3 mm and equal to or smaller than 10 mm. The total length $L_0$ is defined as the length from the supporting part 3 to the tip of the slanted part 21a that punctures the skin.

The total length $L_0$ is normally 8 to 40 nm for conventional subcutaneous or intramuscular administrations. However, the upper limit of the total length $L_0$ of the puncturing part here is chosen shorter than that from the standpoint of securing a desired strength and suppressing an increase of flow path resistance during injection of a drug solution. The lower limit is chosen from the standpoint of effecting a more smooth puncturing into the living body.

The outer diameter of the puncturing part 21 is preferably equal to or larger than 0.1 mm and equal to or smaller than 0.25 mm for a given length $L_1$ starting from the slanted part 21a toward the supporting part 3. The length $L_1$ should be set to $2/3$ or more, or more preferably $4/5$ or more, of the total length $L_0$ if the total length $L_0$ is equal to or longer than 1.5 mm and equal to or shorter than 5 mm. If the total length $L_0$ is longer than 5 mm and equal to or shorter than 15 mm, the length $L_1$ should be set to $3/5$ or more, or more preferably equal to or larger than $3/5$ and equal to or shorter than $4/5$, of the total length $L_0$.

The lower limit of the length $L_1$ is chosen to minimize the sticking resistance by maintaining the outer diameter of the puncturing part 21 small immediately after skin puncturing by the slanted part 21a. The upper limit of the length $L_1$ is chosen from the standpoint of securing sufficient strength and suppressing the increase of the flow path resistance as the time of drug solution injection.

The puncturing part 21 in this embodiment has a distal end 21b that contains the slanted part 21a, a proximal end 21d that has an outer diameter larger than that of the distal end 21b, and a middle part 21c located between the distal end 21b and the proximal end 21d.

The outer diameter of the middle part 21c changes continuously, and smoothly connects the distal end 21b and the proximal end 21d. The inner diameter of the middle part 21c reduces gradually toward the distal end 21b. Therefore, the drug solution 8 is accelerated as it passes through the middle part 21c to flow powerfully into the distal end 21b.

The distal end 21b and the proximal end 21d can both be formed to have substantially constant outer diameters for the entire length as shown in the drawing figures or can be formed to have tapering shapes.

The outer diameter of the anchoring part 22 that extends through the inside of the supporting part 3 is similar to the outer diameter of the proximal end 21d, and should be equal to or larger than 0.3 mm and equal to or smaller than 2 mm, preferably equal to or larger than 0.35 mm and equal to or smaller than 1.5 mm, more preferably equal to or larger than 0.35 mm and equal to or smaller than 1 mm.

The lower limit of the outer diameter of the anchoring part 22 is chosen to be larger than the distal side diameter of the puncturing part 21 from the standpoint of aggressively reducing the flow path resistance during drug solution injection and increasing the area of junction with the supporting part 3 to enhance the junction strength. The upper limit of the outer diameter of the anchoring part 22 is chosen from the standpoint of suppressing the increase of the external dimension of the supporting part 3. As a result, the inner diameter of the anchoring part 22 should preferably be set equal to or larger than 0.20 mm and equal to or smaller than 1.2 mm, preferably equal to or larger than 0.25 mm and equal to or smaller than 1.0 mm, more preferably equal to or larger than 0.25 mm and equal to or smaller than 0.8 mm.

The anchoring part 22 can be formed alternatively to have its inner diameter increasing gradually toward the passage 31 of the supporting part 3. Doing so will further reduce the flow path resistance so that the drug solution 8 is accelerated as it passes through the anchoring part 22 to flow powerfully into the proximal end 21*d*.

A suitable range of wall thickness of the needle part 2 varies with the construction such as outer diameters and materials of the puncturing part 21 and the anchoring part 22. Specifically, a distal side wall thickness of the puncturing part 21 is equal to or larger than 20 μm and equal to or smaller than 50 μm, and a proximal side wall thickness of the puncturing part 21 and a wall thickness of the anchoring part 22 are equal to or larger than 50 μm and equal to or smaller than 400 μm, preferably equal to or larger than 50 μm and equal to or smaller than 250 μm, more preferably equal to or larger than 50 μm and equal to or smaller than 130 μm.

The needle part 2 is made of stainless steel, for example, and is formed by a plastic working process. However, the needle part 2 can alternatively be made of other metals such as titanium, or other materials such as plastics.

The fixing of the needle part 2 to the supporting part 3 is accomplished by an insert forming process or gluing. Since the needle generally has a small outer diameter, its junction to the supporting part is relatively weak and may fall off from the supporting part. To counter this tendency, the outer diameter of the anchoring part 22 that is fixed to the supporting part 3 is chosen to be larger than the distal side outer diameter of the puncturing part 21 in this embodiment.

In other words, the needle part 2 is firmly fixed to the supporting part 3 via the anchoring part 22 having a large diameter to prevent the needle part 2 from falling off. Moreover, since the joint area between the anchoring part 22 and the supporting part 3 is larger, it is easier to securely fix the needle part 2 to the supporting part 3. Therefore, it is easy to manufacture the drug injection needle 10 and the drug injection device 1 despite the fact that the distal side outer diameter of the puncturing part 21 is small.

Next, this embodiment will be described below from the standpoint of the sticking resistance. The sticking resistance is defined by the load experienced in sticking a silicone rubber piece at a speed of 10 mm/sec. The silicone rubber piece is 0.5 mm thick and its hardness, which is detected by a rubber hardness tester (durometer) based on K6253 type A of the Japanese Industrial Standard, is A50 (referring to Section 7619 of the International. Organization for Standardization).

FIG. 6 is an expanded cross-sectional view of the needle part 2 according to example 1 used in the measurement of the sticking resistance. As shown in the drawing, the total length $L_0$ of the puncturing part 21 is 8 mm or 13 mm, and the length $L_1$ of the distal end 21*b* is 2.75 mm.

The outer diameter and the inner diameter of the proximal end 21*d* are 0.35 mm and 0.25 mm respectively, and the outer diameter and the inner diameter of the distal end 21*b* are 0.2 mm and 0.1 mm. The length of the middle part 21*c* in which the outer diameter and the inner diameter gradually reduce is 3.5 mm and the angle between contour line and the axial line shown by the alternating long and short dash line is 1 degree 50 minutes 28 seconds.

Figure 7A:
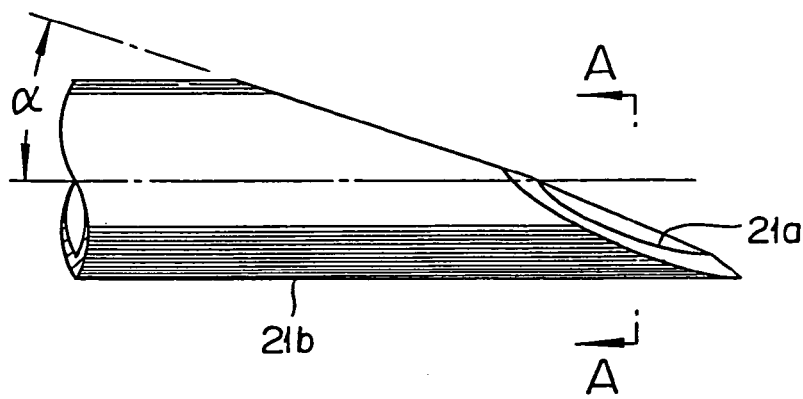
FIG. 7A is a side view of a drug injection needle illustrating a first grinding angle of the drug injection needle.
Figure 7B:
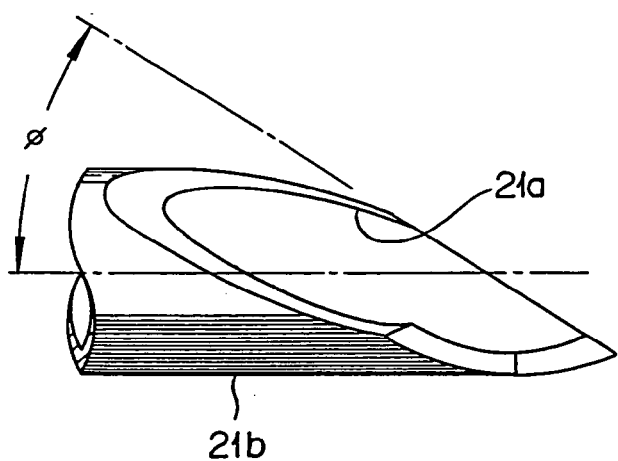
FIG. 7B is a view of a drug injection needle illustrating a second grinding angle of the drug injection needle.
Figure 7C:
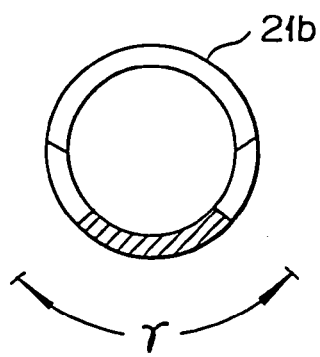
FIG. 7C is a cross-sectional view taken along the section line A-A in FIG. 7A illustrating a cross-sectional angle of the drug injection needle.

A first grinding angle α, a second grinding angle φ, and a cross sectional angle γ of the needle part 2 are 8.5, 18 and 129 degrees respectively. As shown in FIG. 7A, the first grinding angle α is the basic angle formed between the centerline of the distal end 21*b* shown by the alternating long and short dash lines and the slanted part 21*a*. In addition, as shown in FIG. 7B, the second grinding angle φ is the angle formed between the cut surface forming the blade surface of the slanted part 21*a* and the centerline. Further, the cross sectional angle γ is, as shown in FIG. 7C, the angle formed between the edges of the two sides of the blade tip section (referring to Section 7864 of the International Organization for Standardization).

As a reference point, a needle available on the market intended for use on drug injection devices for percutaneous self-administration of insulin solution by diabetes patients was used, with such needle having a constant outer diameter of 0.254 mm and a constant inner diameter of 0.125 mm for the entire length, i.e., a 31 G needle was used. The first grinding angle α, the second grinding angle φ, and the cross sectional angle γ of the 31 G needle were 9, 22 and 130 degrees respectively.

Figure 8:
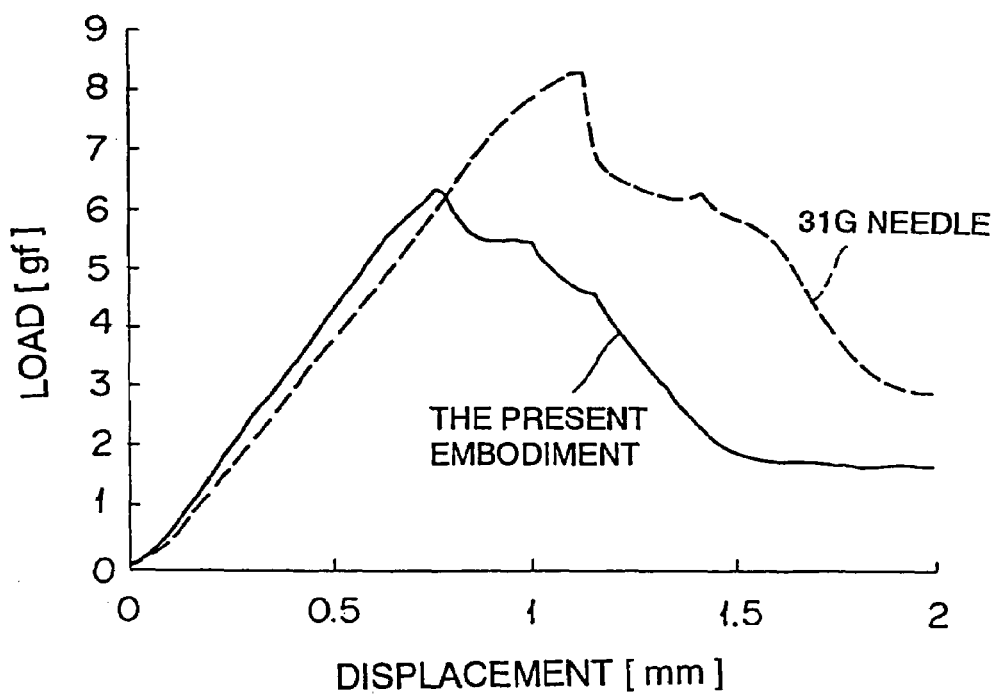
FIG. 8 is a graph showing sticking resistance measurement results of example 1.

FIG. 8 is a graph showing the measurement result of the sticking resistance of example 1, with the vertical axis and the horizontal axis showing the load and the displacement respectively. As can be seen from FIG. 8, the sticking resistance of the needle part 2 according to the present embodiment is markedly smaller than that of the conventional 31G needle in an area where a peak indicates a maximum load.

It can be seen from the graph that the maximum value of the sticking resistance of the conventional needle 31G is 8.4 gf (gram-force) (82.3 mN) and thus exceeds 8 gf (78.4 mN), while the maximum value of the sticking resistance of the needle part 2 is 6.4 gf (62.7 mN) and is thus less than 7 gf (68.6 mN). This evidences that the needle part 2 according to the present embodiment has superior characteristics with respect to the sticking resistance as compared to the 31 G needle and is thus capable of reducing the sticking pain to the patient.

Figure 9:
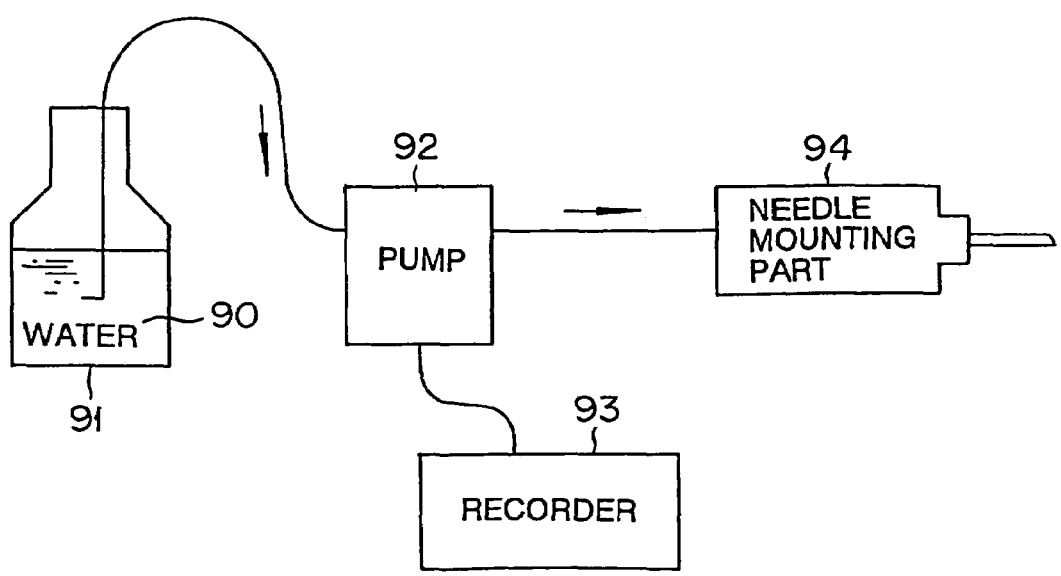
FIG. 9 is a schematic illustration of a flow path resistance measurement system.

Next, the present embodiment will be described below from the standpoint of flow path resistance. The flow path resistance is defined as the driving force required for sustaining a constant flow of 20 μl/sec using water. As shown in FIG. 9, the measuring system for the flow path resistance has a container 91 containing water 90, which is the liquid used for the test, a pump 92 for transferring the suctioned water 90 under a pressure, a recorder 93 for recording the discharge pressure of the pump 92 (i.e., the driving force), and a needle mounting part 94 for detachably attaching the needle part, for which the sticking resistance is measured.

More specifically, the water 90 is pure water produced by a reverse osmosis membrane, and the pump 92 is a metering pump used generally for high-speed liquid chromatography. The needle mounting part 94 and the needle part are detachably connected by way of a screw.

Figure 10:
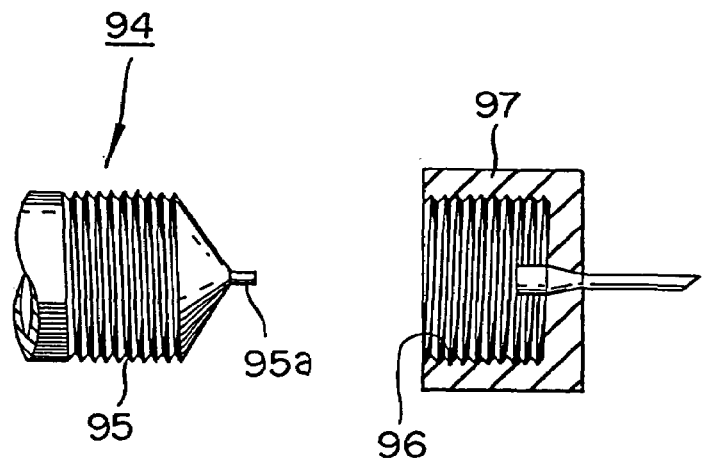
FIG. 10 is a cross-sectional view of explaining a method for connecting a needle mounting part and a needle part according to the flow path resistance measurement system.

Specifically, as shown in FIG. 10, the needle part is connected to a known needle hub 97 with an internally threaded part 96 by way of adhesives or the like, and the internally threaded part 96 is screwed to an externally threaded part 95 formed on the needle mounting part 94. The externally threaded part 95 includes a hollow tube part 95*a*, which is inserted into the proximal end of the needle part to introduce the water 90 into the needle part.

The recorder 93 records the discharge pressure of the pump 92 at a steady state when the flow quantity of the pump 92 is sustained at 20 μl/sec.

The measurement of the flow path resistance was performed for the same needle part 2 (example 1) according to the present embodiment used in the sticking resistance measurement, and was also performed with respect to two kinds of reference needles. One of the reference needles is a 31 G needle that is the same as the needle used in the sticking resistance measurement as stated above, and the other is a 33 G needle having a constant outer diameter of 0.203 mm for the entire length, which corresponds to the outer diameter of the distal end 21b of the puncturing part 21, and a constant inner diameter of 0.105 mm for the entire length.

Figure 11:
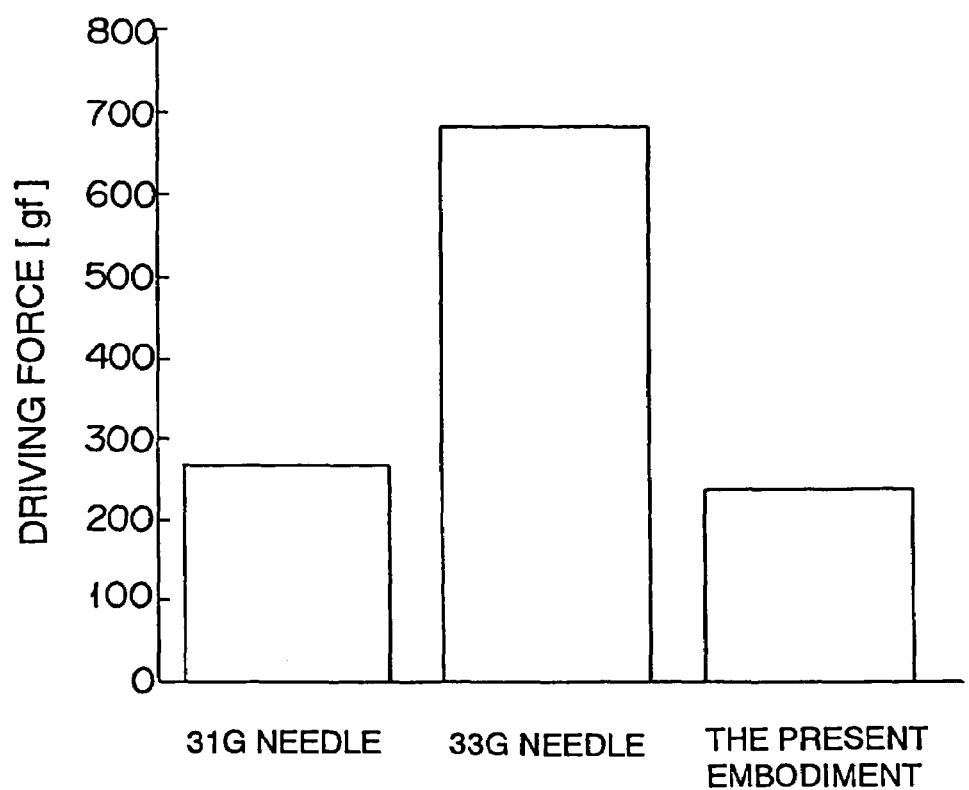
FIG. 11 is a graph showing the results of the flow path resistance measurement of example 1.

FIG. 11 is a graph showing the results of the flow path measurement. As can be seen from the graph, the flow path resistance of the 31 G needle was about 272 gf (2.67 N), the flow path resistance of the 33 G needle was about 690 gf (6.76 N), and the flow path resistance of the needle part 2 according to this embodiment was about 245 gf (2.40 N).

Thus, the flow path resistance of the needle part 2 is less than a half of the flow path resistance of the 33 G (i.e., 350 gf (3.43 N)) despite the fact that the outer diameter of the distal end 21b of the needle part 2 is equivalent to that of the 33 G needle.

More specifically, the 33 G needle exhibits a flow path resistance of approximately 2.5 times the 31 G needle, and the needle part 2 exhibits a flow path resistance of approximately 0.9 times the 31 G needle. Thus, the needle part 2 according to the present embodiment possesses better flow path resistance characteristics than the 31 G and the 33 G needles.

FIG. 12 is a table showing the results of the sticking and flow path resistance measurements for examples 2-12 having different dimensions. As is apparent from these results, one of the needle examples possesses a sticking resistance equal to 7.1 gf, another of the needle examples possesses a sticking resistance of 7 gf, and all other needle examples possess a sticking resistance less than 7 gf. In addition, all of the needle examples possess a flow path resistance less than 350 gf. The needle examples thus all possess superior characteristics.

Next, the method of using the drug injection device 1 will be described. The drug solution 8 is sucked from a container such as a vial directly or via a rubber plug into the internal space 41 of the main body 4 of the drug injection device 1. Then, the puncturing part 21 of the needle part 2 is used to percutaneously make a puncture in the body of the patient, which is the target of the drug solution injection. The distal end 21b of the puncturing part 21 is thinner than the conventional needle. Therefore, it is possible to reduce irritation of the nerves and blood vessels related to the pain and/or damage to the nerves and blood vessels, thus resulting in less pain generation.

By pressing the plunger 5, the drug solution 8 in the internal space 41 is injected through the passage 31 of the supporting part 3, the anchoring part 22 and the puncturing part 21 of the needle part 2 into various parts of the living body of the patient, e.g., intracutaneous and subcutaneous parts, muscles, mucous membranes, or various internal organs.

The anchoring part 22 provides a sufficient junction force against the supporting part 3 as its outer diameter is relatively large. Therefore, there is no possibility of the anchoring part 22 coming off from the supporting part 3. Moreover, the proximal end 21d of the puncturing part 21 provides sufficient strength as its outer diameter is relatively large. Therefore, the puncturing part 21 is prevented from breaking.

The inner diameters of the anchoring part 22 and the proximal end 21d of the puncturing part 21 are relatively large. Therefore, the flow path resistances of the anchoring part 22 and the puncturing part 21 are minimized. Consequently, the force required to press the plunger 5 and push out the drug solution 8 is smaller and the injection of the drug solution 8 is performed smoothly and is thus improved.

Figure 13:
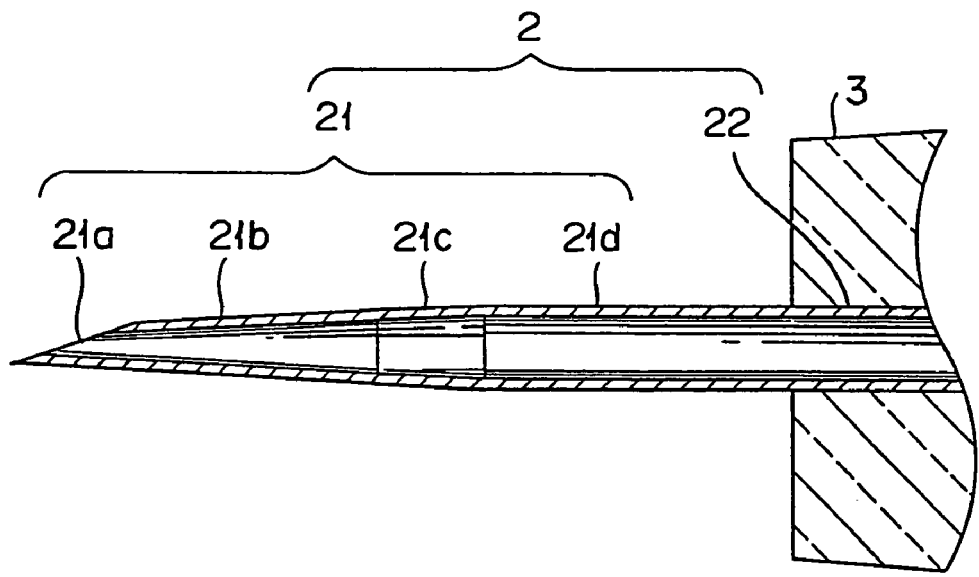
FIG. 13 is a cross-sectional view of a drug injection device according to another embodiment.

It should be understood that this invention is not limited to the particular embodiments shown and described above, but may be changed and modified without departing from the technical concept of this invention. For instance, the shape of the distal end 21b of the puncturing part 21 does not necessarily have to have a constant outer diameter over its entire length. For example, the distal end 21b can have a tapering shape as shown in FIG. 13. The profile lines of the cross-section along the axis of the distal end 21b can be straight or gradually curved.

Figure 14:
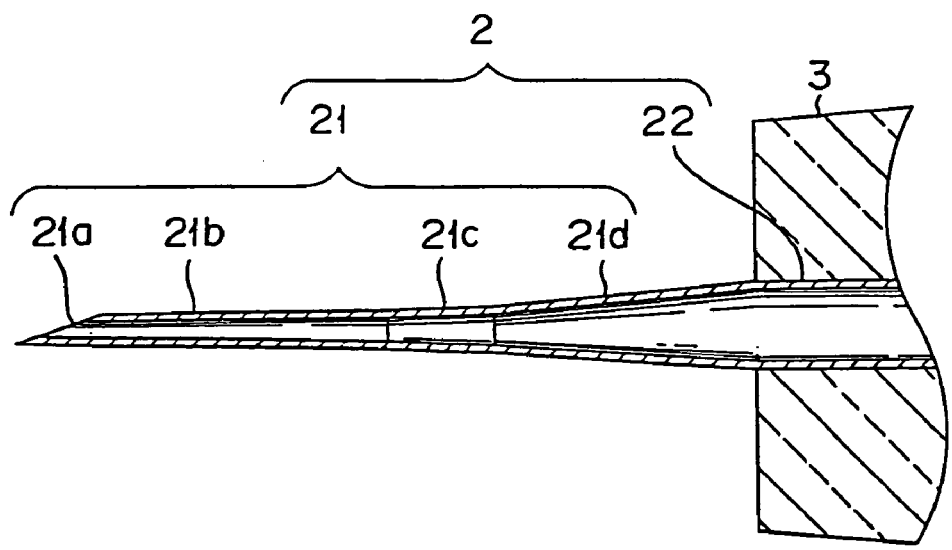
FIG. 14 is a cross-sectional view of a drug injection device according to another embodiment.

As shown in FIG. 14, the outer diameter the puncturing part 21 can be gradually reduced from the proximal end 21d toward the slanted part 21a. The profile lines of the cross-section along the axis of the puncturing part 21 can be straight or gradually curved.

Compared to the construction in which the outer diameter is substantially constant for the entire length of the distal end 21b, the embodiments shown in FIG. 13 and. FIG. 14 allow the outer diameter of the distal end 21b in the vicinity of the slanted part 21a to be smaller to thereby reduce the puncturing pain to the patient.

Moreover, because the internal diameter of the distal end 21b gradually reduces toward the slanted part 21a, the drug solution 8 is accelerated when it passes through the distal end 21b and thus flows out of the slanted part 21a more powerfully.

Although embodiments described above and illustrated in the drawing figures depict the drug injection needle 10 as having only one puncturing part 21, it is possible to arrange to have a plurality of puncturing parts 21 as well. With such an arrangement, it is possible to increase the injection volume of the drug solution 8, so that a more expedient effect of the drug can be anticipated as the drug solution 8 is distributed more efficiently into various parts of the living body.

INDUSTRIAL APPLICABILITY

As described in the above, the outer diameter of the distal end of the puncturing part can be made smaller in comparison with the known prior art practices. For that reason, irritation and damage caused by the puncturing part to blood veins and nerves, and related the pain, can be reduced. Thus, pain to the patient can be decreased. The proximal side outer diameter of the puncturing part is larger than the distal side outer diameter, so that strength sufficient for making a puncture in the living body with the puncturing part can be secured or ensured. Therefore, it is possible to avoid situations in which it is not possible to make a puncture due to breakdown of the puncturing part, for example.

As the outer diameter of the anchoring part that extends through the supporting part has a larger diameter compared to the known design, the joint area between the anchoring part and the supporting part is increased to allow the anchoring part to be fixed on the supporting part more securely. Thus, the liquid injection needle and the liquid injection device can be manufactured more easily despite the fact that the outer diameter of the distal end of the puncturing part is relatively small.

Also, because the inner diameters of the proximal end of the puncturing part and the anchoring part are made larger., the flow path resistance during injection of the liquid into the living body can be reduced. This reduces the force required for injecting the liquid and makes it possible to improve the injection of the fluid into the living body.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A liquid injection needle used for percutaneous self-administration or a dental treatment comprising:
    a hollow needle part for injecting a liquid;
    a supporting part to which the needle part is fixed,
    wherein said hollow needle part comprises
        an anchoring part that extends through an inside of said supporting part and
        a puncturing part that extends from said supporting part for making a puncture in a living body, and said puncturing part comprises
            a distal end,
            a middle part and
            a proximal end,
    wherein said distal end has a distal side outer diameter that is constant over an entire length of the distal end, and said middle part has an outer diameter that gradually reduces toward said distal end to smoothly connect said distal end and said proximal end,
    wherein said distal side outer diameter is equal to or greater than 0.1 mm and equal to or less than 0.25 mm, and a proximal side outer diameter is greater than said distal side outer diameter and equal to or greater than 0.3 mm and equal to or less than 2 mm, a distal side internal diameter is larger than 0.05 mm and smaller than 0.15 mm, and a proximal side internal diameter is equal to or larger than 0.20 mm and equal to or smaller than 1.2 mm,
    wherein said puncturing part has a total length greater than the entire length of the distal end, the total length being equal to or greater than 1.5 mm and equal to or less than 15 mm,
    wherein the entire length of the distal end is ⅔ or more of the total length of the puncturing part when the total length of the puncturing part is equal to or greater than 1.5 mm and equal to or less than 5 mm,
    wherein the entire length of the distal end is ⅗ or more of the total length of the puncturing part when the total length of the puncturing part is greater than 5 mm and equal to or less than 15 mm, and
    wherein said needle part possesses a flow path resistance equal to or less than 350 gram-force under a sustained water flow rate of 20 µl/sec.

2. The liquid injection needle as claimed in claim 1, wherein an outer diameter of said puncturing part gradually decreases from said supporting part toward a tip of said puncturing part.

3. The liquid injection needle as claimed in claim 1, wherein said liquid contains a drug that acts on a living body.

4. The liquid injection needle as claimed in claim 1, wherein the puncturing part possesses a sticking resistance equal to or less than 7 gram-force.

5. A liquid injection device provided with said liquid injection needle as claimed in claim 1, comprising a main body having an internal space adapted to contain said liquid, said supporting part being provided at one end of the main body, said needle part of said liquid injection needle being fixed on said supporting part to communicate with said internal space.

6. The liquid injection needle according to claim 1, wherein when the total length of the puncturing part is greater than 5 mm and equal to or less than 15 mm and the entire length of the distal end is ⅗ or more of the total length of the puncturing part, then the entire length of the distal end is ⅘ or less of the total length of the puncturing part.

7. The liquid injection needle according to claim 1, wherein said distal end includes a slanted part forming a blade tip section, the slanted part comprising a first angle with respect to a centerline of the distal end, a second angle with respect to the centerline of the distal end, and a third angle between edges of the blade tip section.

8. The liquid injection needle according to claim 7, wherein the first angle is 8.5°, the second angle is 18°, and the third angle is 129°.

9. A liquid injection needle used for percutaneous self-administration or a dental treatment comprising:
    a hollow needle part for injecting a liquid;
    a supporting part to which the needle part is fixed,
    wherein said hollow needle part comprises
        an anchoring part that extends through an inside of said supporting part and
        a puncturing part that extends from said supporting part for making a puncture in a living body, and said puncturing part comprises
            a distal end,
            a middle part and
            a proximal end,
    wherein said distal end has a distal side outer diameter that is constant over an entire length of the distal end, said middle part has an outer diameter that gradually reduces toward said distal end to smoothly connect said distal end and said proximal end, and said proximal end has a constant proximal side outer diameter,
    wherein said distal side outer diameter is equal to or greater than 0.1 mm and equal to or less than 0.25 mm, and the proximal side outer diameter is greater than said distal side outer diameter and equal to or greater than 0.3 mm and equal to or less than 2 mm, a distal side internal diameter is larger than 0.05 mm and smaller than 0.15 mm, and a proximal side internal diameter is equal to or larger than 0.20 mm and equal to or smaller than 1.2 mm,
    wherein said puncturing part has a total length greater than the entire length of the distal end, the total length being equal to or greater than 1.5 mm and equal to or less than 15 mm,
    wherein the entire length of the distal end is ⅔ or more of the total length of the puncturing part when the total length of the puncturing part is equal to or greater than 1.5 mm and equal to or less than 5 mm,
    wherein the entire length of the distal end is ⅗ or more of the total length of the puncturing part when the total length of the puncturing part is greater than 5 mm and equal to or less than 15 mm, and
    wherein said needle part possesses a flow path resistance equal to or less than 350 gram-force under a sustained water flow rate of 20 µl/sec.

* * * * *